(12) United States Patent
Patch

(10) Patent No.: US 10,758,127 B2
(45) Date of Patent: Sep. 1, 2020

(54) SYSTEMS AND METHODS FOR RADIATION BEAM RANGE VERIFICATION USING SONIC MEASUREMENTS

(71) Applicant: Sarah Kathryn Patch, Milwaukee, WI (US)

(72) Inventor: Sarah Kathryn Patch, Milwaukee, WI (US)

(*) Notice: Subject to any disclaimer, the term of this patent is extended or adjusted under 35 U.S.C. 154(b) by 0 days.

(21) Appl. No.: 16/320,951

(22) PCT Filed: Jul. 20, 2017

(86) PCT No.: PCT/US2017/043125
§ 371 (c)(1),
(2) Date: Jan. 25, 2019

(87) PCT Pub. No.: WO2018/022431
PCT Pub. Date: Feb. 1, 2018

(65) Prior Publication Data
US 2019/0175947 A1    Jun. 13, 2019

Related U.S. Application Data

(60) Provisional application No. 62/366,613, filed on Jul. 25, 2016.

(51) Int. Cl.
*A61B 5/00* (2006.01)
*G06T 7/00* (2017.01)
(Continued)

(52) U.S. Cl.
CPC .......... *A61B 5/0093* (2013.01); *A61B 5/0095* (2013.01); *A61B 5/4848* (2013.01);
(Continued)

(58) Field of Classification Search
CPC .......... A61B 5/0095; A61B 2562/0204; A61B 2505/05; A61B 5/01; A61B 5/7257;
(Continued)

(56) References Cited

U.S. PATENT DOCUMENTS 8,481,951 B2 * 7/2013 Jongen ................. A61N 5/1048
250/363.05
9,186,525 B2 * 11/2015 Prieels ................. A61N 5/1048
(Continued)

FOREIGN PATENT DOCUMENTS

CN     108478936 A  *  9/2018  ............... A61N 5/10
CN     108535696 A  *  9/2018  ............... G01S 5/22
(Continued)

OTHER PUBLICATIONS

English translation of CN108535696A. Publication year: 2018.*
(Continued)

*Primary Examiner* — Amanda Lauritzen Moher
(74) *Attorney, Agent, or Firm* — Andrus Intellectual Property Law, LLP

(57) ABSTRACT

Systems and methods for estimating the location of a wave source based upon low frequency measurements acquired using multiple receivers. In one aspect, a method for estimating an end range of a radiation beam delivered to a target is provided. The method includes controlling a radiation treatment system to deliver a radiation beam inducing at least one low frequency thermoacoustic wave inside a target, and detecting, using receivers positioned about the target, sonic signals corresponding to the at least one low frequency thermoacoustic wave. The method also includes analyzing the sonic signals to determine differences in times-of-flight associated with different receivers, and estimating an end range of the radiation beam by correlating the differences in
(Continued)

times-of-flight. The method further includes generating a report indicative of the end range of the radiation beam.

25 Claims, 13 Drawing Sheets

(51) Int. Cl.
*G01N 21/17* (2006.01)
*A61N 5/10* (2006.01)
*A61B 8/08* (2006.01)
*A61B 5/01* (2006.01)

(52) U.S. Cl.
CPC .......... *A61B 5/7203* (2013.01); *A61B 5/7257* (2013.01); *A61B 8/085* (2013.01); *A61N 5/1048* (2013.01); *A61N 5/1067* (2013.01); *G01N 21/1702* (2013.01); *G06T 7/0012* (2013.01); *A61B 5/01* (2013.01); *A61B 2505/05* (2013.01); *A61B 2562/0204* (2013.01); *A61N 2005/1058* (2013.01); *A61N 2005/1087* (2013.01); *G01N 2021/1708* (2013.01)

(58) Field of Classification Search
CPC ..... A61B 5/4848; A61B 5/0093; A61B 8/085; A61B 5/7203; G01N 21/1702; G01N 2021/1708; G06T 7/0012; A61N 5/1067; A61N 5/1048; A61N 2005/1087; A61N 2005/1058
See application file for complete search history.

(56) References Cited

U.S. PATENT DOCUMENTS

| | | | | |
|---|---|---|---|---|
| 2008/0221647 | A1* | 9/2008 | Chamberland | A61B 5/0095 607/88 |
| 2011/0160738 | A1* | 6/2011 | McIntosh | A61B 8/565 606/102 |
| 2012/0281895 | A1 | 11/2012 | Chono et al. | |
| 2015/0173715 | A1* | 6/2015 | Raghavan | A61B 8/46 600/440 |
| 2016/0113507 | A1* | 4/2016 | Reza | G01N 21/1717 |
| 2016/0178583 | A1 | 6/2016 | Ntziachristos et al. | |
| 2017/0164835 | A1* | 6/2017 | Wiest | A61B 8/5269 |
| 2018/0270474 | A1* | 9/2018 | Liu | G06K 9/00201 |
| 2019/0150881 | A1* | 5/2019 | Maharbiz | A61B 5/076 |

FOREIGN PATENT DOCUMENTS

| | | |
|---|---|---|
| JP | 2006 158678 A | 6/2006 |
| WO | WO 2014/179430 A2 | 11/2014 |
| WO | WO 2016/000777 A1 | 1/2016 |
| WO | WO 2016/009042 A1 | 1/2016 |

OTHER PUBLICATIONS

English translation of CN108478936A. Publication year: 2018.*
Otero et al. "Acoustic Localization of Bragg Peak Proton Beams for Hadrontherapy Monitoring." Sensors (Basel) 19(9): 2019.*
Patch et al. "Two-stage ionoacoustic range verification leveraging Monte Carlo and acoustic simulations to stably account for tissue inhomogeniety and accelerator-specific time structure—A simulation study." Med. Phys 45(2): 2018.*
Patch et al. "Thermoacoustic range verification using a clinical ultrasound array provides perfectly co-registered overlay of Bragg peak onto an ultrasound image." Phys. Med. Biol. 61(15): 2016.*
Lehrack et al. "Ionoacoustic detection of swift heavy ions." 2019.*
Hickling et al. "Ionizing radiation-induced acoustics for radiotherapy and diagnostic radiology applications." Med. Phys. 45(7): 2018.*
Alsanea. "Feasibility of Pulsed Proton Induced Acoustics for 3D Dosimetry." Purdue e-Pubs: 2014.*
Takayanagi et al. "A novel range-verification method using ionoacoustic wave generated from spherical gold markers for particle-beam therapy: a simulation study." Sci. Rep. 9: 2019.*
Otero et al. "Acoustic Bragg peak localization in proton therapy treatment: Simultion studies." Conference: 6th International Electronic Conference on Sensors and Applications: 2019.*
International Patent Application No. PCT/US2017/043125, International Search Report and Written Opinion dated Oct. 16, 2017, 14 pgs.
International Patent Application No. PCT/US2017/043125, International Preliminary Report on Patentability dated Oct. 15, 2018, 42 pgs.
Wang (2009), "Multiscale photoacoustic microscopy and computed tomography," Nat Photonics. 2009; 6,23 3(9):503-509.
Xu et al. (2005), "Universal back-projection algorithm for photoacoustic computed tomography," Phys 1-42, Rev E Stat Nonlin Soft Matter Phys. 2005; 71(1, pt 2):016706.
Patch et al. (2016) "Thermoacoustic range verification using a clinical ultrasound array provides perfectly co-registered overlay of the Bragg peak onto an ultrasound image", Physics in Medicine and Biology, Institute of Physics Publishing, Bristol GB, vol. 61, No. 15, Jul. 6, 2016 (Jul. 6, 2016), pp. 5621-5638.
European Patent Application No. 17835006.2, Extended European Search and Opinion dated Dec. 4, 2019, 9 pages.

* cited by examiner

SYSTEMS AND METHODS FOR RADIATION BEAM RANGE VERIFICATION USING SONIC MEASUREMENTS

CROSS-REFERENCE TO RELATED APPLICATIONS

This application is a 35 U.S.C. §filing of International Application No. PCT/US2017/043125, filed Jul. 20, 2017, which is based on, which claims priority to U.S. Ser. No. 62/366,613 filed Jul. 25, 2016 and entitled "Method and System for Deriving Accurate, High Resolution Time of Flight Estimates from Multiple Correlated, but Low Resolution Measurements", each of which is incorporated by reference in its entirety.

BACKGROUND

The present disclosure generally relates to systems and methods for locating wave sources, and in particular, to systems and methods for thermoacoustic range verification in ion therapy.

Ion therapy takes advantage of the energy deposition profile of high energy ions to provide highly conformal irradiation of tumors while sparing critical structures. Specifically, an ion beam has a finite penetration depth inside a patient, and depends on the ion energies. In contrast to conventional photon radiotherapy, most of the radiation dose of a mono-energetic ion beam is delivered within a short distance of its end range in tissue, also known as the Bragg peak. Superficial tissues receive less radiation dose compared to those near the Bragg peak. In addition, the dose profile drops dramatically beyond the Bragg peak, with those tissues receiving practically no radiation dose thereafter. Such dose deposition characteristics allow high doses to be delivered to deep-seated tumors with reduced normal tissue doses and toxicities. To provide volume coverage, often a combination of multiple proton beams with different energies are utilized, resulting in a spread-out Bragg peak with increased dose received by superficial tissues.

Regardless of whether single or multi-energy beams are used, ion range inaccuracies are often of concern due to the steep dose drop-off near the Bragg peak, which can reduce target coverage and increase toxicities to critical structures. End range inaccuracies can occur from positioning errors, changes or movement in a patient's anatomy and patient motion. In some cases, specific anatomical features, such as large boney structures or gas pockets in the abdomen, can move in or out of the beam path and introduce large uncertainties due to significant differences in beam stopping power.

Although positioning is verified prior to treatment and interlocks can halt treatment immediately upon detecting equipment failure, no safety mechanism exists to defend against anatomical changes and patient motion during treatment. As a result, many proton treatment plans are developed to favor certain beam arrangements that are robust to errors induced by range inaccuracies. For example, prostate treatments typically use parallel-opposed lateral beams. However, many such plans can often be suboptimal with respect to the overall target coverage and exposure of healthy tissue, thereby decreasing treatment effectiveness and increasing toxicity risk.

Therefore, several techniques have been developed with the goal of estimating or inferring ion range prior to, during and after treatment field delivery. For instance, one approach utilizes short-lived isotopes that are produced by nuclear interactions of an ion beam with tissue. The isotopes decay to positrons that annihilate and generate coincident gamma rays that are measurable with a PET scanner. By overlaying PET data on CT images, a good indicator of the delivered radiation can be obtained. However, such passive scattering methods are only valid for pretreatment verification with selected beam angles. Also, although prompt gamma emissions can provide fast and real-time feedback, they cannot yet achieve millimeter accuracy due to the decaying nature of the isotopes and the resolution limits on PET imaging. In addition, an automated method for correlating PET data to underlying anatomy in CT images acquired days prior to treatment is slow and precludes online range verification. Furthermore, ion range is determined based on room coordinates, which are subject to setup uncertainty and intrafractional motion when registered to underlying anatomy.

Another approach for range verification relies on the thermoacoustic effect. For instance, when an ion beam is incident on a tissue, thermoacoustic pressure waves are generated due to the localized energy deposition near the Bragg peak. Although in principle such pressure waves may be measurable using ultrasound detection techniques, many challenges remain for translating the approach to a clinical setting. For example, in soft tissue, an instantaneous delivery of 2 Gy generates a pressure of 200 Pa at the Bragg peak, whereas a reduced dose of 1 cGy generates only 1 Pa. Pressure amplitudes, however, decay with distance from the Bragg peak, and detectors must therefore be positioned relatively close. Also, since tissues are subject to radiation dose constraints, there are limits on measurable pressure amplitudes, as well as the ability to perform significant signal averaging. Furthermore, range verification also requires dose depositions to be fast enough to ensure that pressure is generated and detected before it can dissipate.

In addition, ion scattering blurs the location of a thermoacoustic source and bandlimits signals detected by transducers located laterally or distally. Specifically, although ions scatter less than photons in soft tissue, a thermoacoustic source is determined longitudinally by the linear energy transfer (LET) or Bragg curve, and laterally by beam diameter, both of which often have full width at half maximum (FWHM) greater than about 7.5 mm. Acoustic travel time across a 7.5 mm beam is approximately 5 µs, which bandlimits thermoacoustic emissions below 200 kHz. Additionally, spill times of clinical ion therapy systems currently exceed 6 µs, further bandlimiting spectra and suppressing pressure amplitudes. Simulations of 230 MeV proton beams in water targets indicate thermoacoustic emissions are bandlimited below 150 kHz, assuming instantaneous deposition. Finally, resolving the range or Bragg peak location with better than 3 mm accuracy requires methods beyond the scope of typical inverse source techniques, which are typically accurate to within one-half wavelength. The acoustic wavelength corresponding to 150 kHz is 10 mm, so 5 mm accuracy is expected from traditional one-way beamforming of thermoacoustic emissions.

Although ion therapy has long been recognized as advantageous for treating various adult and pediatric tumors, including those associated with the base of the neck, spine, eye, prostate and others, inadequate range verification has limited its clinical utility. Therefore, there is an urgent need to develop accurate and fast range verification for the treatment of many cancers.

SUMMARY

The present disclosure overcomes the aforementioned drawbacks by providing systems and methods for estimating radiation beam range in a target subject to radiation treatment. As will be described, a novel approach is introduced in which multiple low resolution measurements may be utilized to accurately estimate a radiation beam's end range or Bragg peak. Specifically, signals associated with induced low frequency thermoacoustic waves may be detected using multiple receivers arranged about the target, and the measurements combined to estimate the position of the Bragg peak. In some aspects, low frequency thermoacoustic wave measurements may be correlated with reference information, including simulation data, to obtain more accurate end range estimates. In this manner, a treatment or treatment plan may be advantageously adjusted, allowing for improved patient outcomes.

In accordance with one aspect of the disclosure, the present invention is a method for estimating an end range of a radiation beam delivered to a target. The method includes controlling a radiation treatment system to deliver a radiation beam inducing at least one low frequency thermoacoustic wave inside a target, and detecting, using receivers positioned about the target, sonic signals corresponding to the at least one low frequency thermoacoustic wave. The method also includes analyzing the sonic signals to determine differences in times-of-flight associated with different receivers, and estimating an end range of the radiation beam by correlating the differences in times-of-flight. The method further includes generating a report indicative of the end range of the radiation beam.

In accordance with another aspect of the disclosure, a method for estimating an end range of a radiation beam delivered to a target is provided. The method includes controlling a radiation treatment system to deliver a radiation beam inducing at least one low frequency thermoacoustic wave inside a target, and detecting, using receivers positioned about the target, sonic signals corresponding to the at least one low frequency thermoacoustic wave. The method also includes computing a preliminary end range estimate of the radiation beam using the sonic signals, and analyzing the sonic signals to determine time-of-flight information corresponding to different receivers. The method further includes computing, based on the preliminary end estimate and time-of-flight information, a corrected end range estimate of the radiation beam, and generating a report indicative of the corrected end range estimate.

In accordance with yet another aspect of the disclosure, a system for estimating an end range of a radiation beam delivered to a target. The system includes a sonic system having a plurality of receivers configured to acquire sonic signals from a target. The system also includes a controller programmed to control a radiation treatment system to deliver a radiation beam inducing at least one low frequency thermoacoustic wave inside a target, and detect, using receivers positioned about the target, sonic signals corresponding to the at least one low frequency thermoacoustic wave. The controller is also programmed to analyze the sonic signals to determine differences in times-of-flight associated with different receivers, and estimate an end range of the radiation beam by correlating the differences in times-of-flight. The controller is further programmed to generate a report indicative of the end range of the radiation beam.

In accordance with yet another aspect of the disclosure, a method for localizing a wave source is provided. The method includes detecting, using multiple receivers positioned about a wave source, wave signals corresponding to the wave source, and computing a preliminary estimate of a location of the wave source using the wave signals. The method also includes analyzing the wave signals to determine time-of-flight information, including relative times-of-flight, corresponding to different receivers, and correlating the time-of-flight information corresponding to the different receivers to compute a corrected estimate of the location of the wave source. The method further includes generating a report indicative of the corrected estimate.

In accordance with yet another aspect of the disclosure, a system for estimating an end range of a radiation beam delivered to a target is provided. The system includes a sonic system having a plurality of receivers configured to acquire sonic signals from a target and a controller programmed to control a radiation treatment system to deliver a radiation beam inducing at least one low frequency thermoacoustic wave inside a target. The controller is also programmed to detect, using receivers positioned about the target, sonic signals corresponding to the at least one low frequency thermoacoustic wave, compute a preliminary end range estimate of the radiation beam using the sonic signals, and analyze the sonic signals to determine time-of-flight information corresponding to different receivers. The controller is further programmed to compute, based on the preliminary end estimate and time-of-flight information, a corrected end range estimate of the radiation beam, and generate a report indicative of the corrected end range estimate.

In accordance with yet another aspect of the disclosure, a method for localizing a wave source is provided. The method includes detecting, using receivers positioned about the wave source, low frequency wave signals corresponding to a range and computing, using the wave signals, a preliminary estimate locating the wave source. The method also includes analyzing the wave signals to determine time-of-flight information, including relative times-of-flight, corresponding to different receivers, and computing, based on the preliminary estimate and time-of-flight information, a corrected wave source location. The method further includes generating a report indicative of the corrected wave source location.

The foregoing and other advantages of the invention will appear from the following description.

BRIEF DESCRIPTION OF THE DRAWINGS

The present invention will hereafter be described with reference to the accompanying drawings, wherein like reference numerals denote like elements.

DETAILED DESCRIPTION

Figure 1:
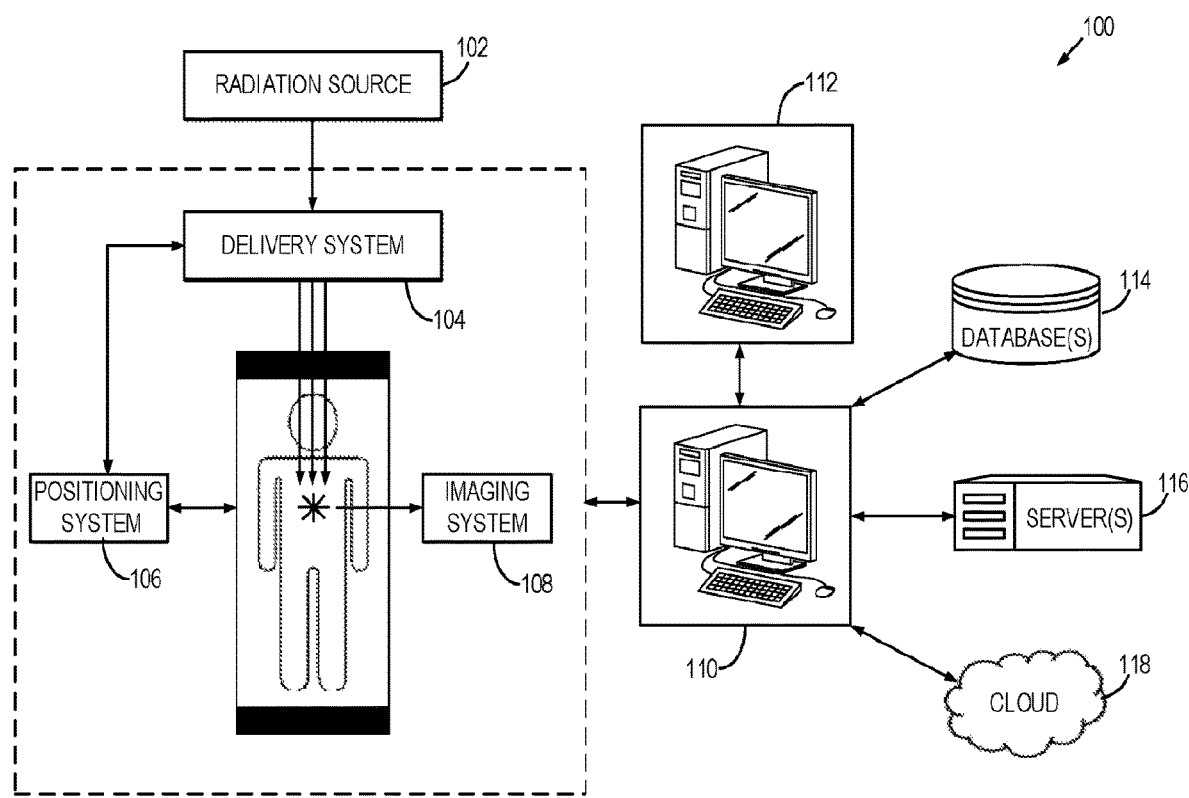
FIG. 1 is a schematic diagram of an example radiation treatment system, in accordance with aspects of the present disclosure.

Although proton and other ion beams can potentially deliver much higher doses to tumors while keeping dose to normal tissues low, they are more sensitive to uncertainties compared with photon-based treatments. Uncertainties can lead to local treatment failure and normal tissue over-dose, which can significantly increase the risk of severe adverse effects and secondary cancers. In some cases, the possibility of adverse effects can compromise or reduce the effectiveness of therapy because suboptimal dose reductions are needed to minimize risks to a patient. By addressing beam inaccuracies, treatment can be improved to decrease morbidity and result in better quality of life for patients. Therefore, the present disclosure introduces a novel approach for estimating radiation beam range in a target subject to radiation treatment. Although reference is made herein with regard to proton therapy, it may be readily appreciated that the present approach or portions thereof may be broadly applicable to any ion beam therapy, as well as to x-ray radiation therapy.

As described, ionizing radiation can produce detectable thermoacoustic waves in a target. However, unlike thermoacoustic or photoacoustic imaging applications that utilize non-ionizing energy to heat tissue and generate thermoacoustic signals, radiation therapies includes limits on how much dose a patient or target can receive. This in turn limits the measurable signals as well ability to perform signal averaging. Also, a radiation beam also suffers from "straggle" inside the target due to scattering. Therefore, the amplitude and bandwidth of a low resolution measurement of a low frequency thermoacoustic wave induced by a pulsed proton beam, for instance, would be insufficient to accurate estimate the proton range using standard ultrasound hardware and beamforming techniques.

In contrast to previous technologies, it is recognized herein that multiple low resolution signals associated with induced low frequency waves, such as thermoacoustic waves, may be judiciously utilized to accurately estimate a radiation beam's end range or Bragg peak. To this end, in some aspects, a beamforming technique may be applied to the measurements to obtain a preliminary end range estimate. The preliminary end range estimate may then be corrected using time-of-flight information derived from various measurements, as well as a priori information obtained from simulated thermoacoustic emissions, for example. Specifically, time-of-flight information may be obtained using measurements from different receivers, where measured signals of an induced low frequency thermoacoustic wave are correlated in time and shifted in the time domain depending upon receiver positions. This results in phase shifts in the Fourier domain that may be used to estimate differences in times-of-flight between each of the measurements with an accuracy that can surpass the classical half wavelength resolution limit of any individual measurement.

Although the present disclosure makes reference to estimating a radiation beam's end range based on induced thermoacoustic waves, it is envisioned herein that the present approach may be applied much more broadly. For instance, the present approach of utilizing multiple low-resolution measurements, which are correlated in some known fashion, to localize wave sources such as mechanical or electromagnetic sources, with a resolution that is higher than what would be achievable from individual low-resolution measurements, may be applied to sonar, radar and other applications. Low frequency signals travel further than those at higher frequencies, and so the present approach may be used to improve a distance versus resolution trade off in acoustics, sonar, and also electromagnetic and radar applications, for instance. To this end, multiple detectors may be integrated along the length of a submarine, a satellite, an airplane, and so on, and the present approach may be applied to localize various sonic and other sources. In addition, the present approach may be extended two-way range estimation methods, which transmit as well as receive low frequency signals.

As used in the present disclosure, terms such as "about" or "approximately" when used in reference to a numerical value or numerical range may generally include values up to 20% above or below the stated nominal value or range values.

As used in the present disclosure, the term "low frequency" generally includes a frequency range spanning DC up to approximately 300 kHz.

As used in the present disclosure, the term "sonic signals" may generally include infrasound, acoustic, and ultrasound signals.

As used in the present disclosure, the term "wave source" may generally include any mechanical or electromagnetic source producing infrasound, acoustic, ultrasound and electromagnetic signals.

As used in the present disclosure, the term "radiation beam" may generally refer to a pulsed, continuous, or semi-continuous stream of ionizing electromagnetic radiation or energetic charged particles.

Referring particularly to FIG. 1, a radiation treatment system 100, in accordance with aspects of the present disclosure, is shown. The radiation treatment system 100 may be an ion therapy system, such as a proton therapy system, and others. As shown, the radiation treatment system 100 may generally include a radiation source 102, such as a cyclotron, synchrotron and so on, a delivery system 104 and a positioning system 106. In accordance with aspects of the present disclosure, the radiation treatment system 100 may also include an imaging system 108.

Specifically, the delivery system 104 is configured to shape and deliver radiation from the radiation source 102, and may include various components and hardware, such as magnets, apertures, filters, collimators, scatterers or scattering elements, attenuators, choppers, and so on, for controlling the profiles, shapes, angles of incidence and exposure times of provided radiation. The delivery system 104 may also include a treatment console, a computer, as well as other components or hardware. In some aspects, the delivery system 104 may be configured to deliver a pulsed radiation beam, such as a pulsed proton beam, with a predetermined spatial, temporal and energy profile.

The positioning system 106 is configured to move the patient or target relative to incident radiation. In some implementations, the positioning system 106 may also be configured to control the position of the patient relative to the imaging system 108. To this end, the positioning system 106 may be configured to move the patient to the imaging system 108, or vice versa, or both.

In one implementation, the imaging system 108 includes a sonic system configured to transmit and receive various sonic signals to and from a target, such as an ultrasound system. The imaging system 108 may also include other imaging capabilities, such as computed tomography, emission tomography, magnetic resonance, and other imaging capabilities. In particular, the sonic system may include a sonic probe assembly that is configured to be coupled to patient or a target to transmit and receive the sonic signals. Specifically, the sonic probe assembly may include a number of transmitters and receivers configured as linear arrays, curved arrays, curvilinear arrays, phased arrays, individual elements or combinations thereof. In some implementations, the sonic probe assembly is configured to acquire signals from a number positions about the target. In a non-limiting example, the sonic probe assembly may be configured to acquire signals from a number of positions located laterally and distally relative to a radiation beam direction.

In some implementations, receivers on the sonic probe assembly are configured to detect various sonic signals corresponding to thermoacoustic waves induced in the target by an applied radiation beam or beam pulse. As such, receivers on the sonic probe assembly may be configured to detect signals in a frequency range approximately between DC and 300 kHz, for example, although other frequencies may be possible. In addition, transmitters and receivers on the sonic probe assembly may also be configured to acquire signals for generating one or more ultrasound images. As such, the transmitters and receivers may be configured to transmit and receive signals in a frequency range approximately between 1 and 20 MHz, although other frequencies may be possible. In some embodiments, the sonic probe assembly and/or sonic system may also include additional elements and circuitry for shaping and processing detected sonic signals, such as amplifiers, filters, voltmeters, current meters, digital scopes, spectrometers, and so on.

As shown, the radiation treatment system 100 may also include a controller 110, in communication with the delivery system 104, the positioning system 106, and the imaging system 108, that is configured to control a radiation treatment. Generally, radiation treatment involves the execution of a treatment plan produced offline on a planning workstation 112. The treatment plan commonly includes multiple treatment fields whose shape and direction of incidence, along with the beam energy and exposure time, determine the dose and dose distribution delivered to a target. As such, the controller 110 is configured to receive the treatment plan from the planning workstation 112 and direct the execution of the treatment plan received. In some aspects, the controller 110 is also configured to carry out various quality control steps, either autonomously or in combination with operator input, including positioning verification, dosing, and others.

As shown in FIG. 1, the controller 110 may be a computer, a workstation, a network server, a mainframe or any other general-purpose or application-specific computing system. The controller 110 may also be part of or communicate with a portable device, such as a mobile phone, laptop, tablet, personal digital assistant ("PDA"), multimedia device, or any other portable device. As such, the controller 110 may also operate as part of, or in collaboration with one or more computers, systems, devices, machines, mainframes, servers and the like. The controller 110 may operate autonomously or semi-autonomously, receiving instructions from a memory, a user, as well as any other source logically connected thereto, such as another networked computer, device or server. In this regard, the controller 110 may be any computing device, apparatus or system having one or more processing units, and designed to integrate a variety of capabilities and functionalities, as well as configured for carrying out steps in accordance with aspects of the disclosure. Example processing units may include CPUs, GPUs and the like.

In addition to being connected to the planning workstation 112 and treatment console of the delivery system 104, the controller 110 may also be communication with various database(s) 114, server(s) 116, the cloud 118, and various other external computers, systems and devices. As such, the controller 110 may be configured to exchange a wide variety of information and data. Specifically, the database 114 may include simulation and measurement data and information, generated either offline or online, related to thermoacoustic emissions for different beams configurations. Simulation data, for instance, may be obtained using Monte Carlo or other computational methods, while measurement data may be obtained using various emissions detections techniques and radiation beam configurations. In one non-limiting example, the database(s) 114 may include tables and other representations identifying end ranges and dose maps and associated thermoacoustic emissions that correspond to selected beam numbers, energies, angles, and so on.

Some modern treatment planning algorithms are based upon Monte Carlo simulations, and advantageous implementations herein may utilize those simulations. Dose maps generated by Monte Carlo simulations and the planning CT volume may be integrated with acoustic software, for example k-Wave, to simulate thermoacoustic emissions. Emissions may be simulated for each planned beam and also beams which over- and under-shoot the plan by several millimeters. This could be achieved, for example, by simulating beams with ranges approximately ±5, 10, 15 mm, and so on, water equivalent paths relative to each planned beam. Alternatively, beam energies could be incremented from the treatment plan by ±1, 2, 3 MeV, and so on.

In some implementations, the controller 110 may be configured to access patient data from the imaging system 108, the databases(s) 114, the server(s) 116, the cloud 118 and elsewhere. Patient data may, for example, include various representations or images of the patient, such as ultrasound, CT, MR, or PET images, information related to target structures, critical structures, treatment plans, and on, as well as patient characteristics and medical history. In some aspects, the controller 110 may also be configured to access and process sonic signal data, acquired before, during or after a radiation treatment.

The controller 110 may include various input elements for receiving data and information. Example input elements may include flash-drives, CD or DVD drives, USB or micro-USB inputs, HDMI inputs, an Ethernet or WIFI connection, and other inputs for receiving computer-readable media, data or signals. The controller 110 may also include input elements configured to receive user selections. Example input elements may include a mouse, keyboard, touchpad, touch screen, buttons, and the like. The controller 110 may also include various output elements for providing a report to a user, as well as to other systems or devices. Example output elements include displays, printers, and so on. The controller 110 may also include one or more memory elements. Such memory elements may include transitory and non-transitory, computer-readable storage media having stored therein instructions, in the form of software, firmware, or programming, for processing various data and information, in accordance with aspects of the present disclosure.

In some implementations, non-transitory, computer-readable storage media include instructions that, when executed by one or more processing units of the controller 110, or another system, may estimate an end range of a radiation beam delivered to a target or a location of a sonic source. Specifically, the controller 110 may be configured to control the delivery system 104 to provide radiation beams inducing low frequency thermoacoustic waves inside the target. The provided radiation beam may include a scout beam as part of a quality assurance protocol. Alternatively, or additionally, the provided radiation beam may be a part of a treatment plan. As an example, the radiation beam may include a proton or ion beam pulse. The controller 110 may then receive and process data corresponding to the low frequency thermoacoustic waves induced by the radiation beam. To this end, the controller 110 may control the acquisition of sonic signals using the imaging system 108.

As described, multiple receivers arranged about and/or within the target may be utilized to acquire the sonic signals. The signals may then be analyzed by the controller 110 to estimate an end range of a radiation beam or a location of a sonic source. In addition, a controller 110 may also verify the estimated end range position or source position relative to a target position. A determination can then be made by the controller 110 whether a treatment plan needs to be adapted, a treatment halted or a patient repositioned, or another adjustment made. The determination may be made based on whether a difference or shift between a beam's estimated end range position, or source position, and a target position exceeds a predetermined threshold value. In some aspects, the threshold value may depend on the specific targeted and critical structures in the body of a patient. In one example, the threshold value may be 5 mm or more, while in another example, the threshold value may be less than 5 mm.

In some implementations, the controller 110 may be configured to correlate measurements obtained from different receivers to estimate an end range. In particular, the controller 110 may determine a time-of-flight to each receiver using the induced low frequency thermoacoustic wave. Herein, the time-of-flight represents the travel time of an induced or non-induced wave from a source position to a receiver position, the source position being associated with substantial radiation dose deposition, or Bragg peak, of a radiation beam, for example. In some aspects, relative differences or shifts between the times-of-flight may also be determined by the controller 110, for example, by applying a Fourier Shift theorem. The controller 110 may then estimate an end range of a radiation beam by correlating determined times-of-flight or time-of-flight differences. In some aspects, the controller 110 may take into account time lags in electronics and signal transit time through receivers. As described, the controller 110 may carry out a similar analysis to determine the location of a sonic source by combining various sonic measurements.

In other implementations, the controller 110 may carry out a two-step process to estimate an end range of a radiation beam from sonic signals. In a first step, a fast estimate may be obtained by applying a beamforming technique to signals corresponding to one or more receivers. For example, one-way beamforming may be used to reconstruct the Bragg peak. In a second step, the beamformed estimate(s) of the end range may be refined or corrected by comparing measured sonic signals to a reference or database having stored therein various a priori information and data, including thermoacoustic emission simulation and measurement data.

As mentioned, the controller 110 is configured to direct or control the acquisition of sonic signals using the imaging system 108. The controller 110 may then use the acquired signals to reconstruct one or more images. In one non-limiting example, the controller 110 may reconstruct 1D, 2D, 3D or 4D ultrasound images of an irradiated target. In some aspects, a two-way beamforming technique may be applied to generate the images. The controller 110, or another suitable system, may be configured to control the acquisition and reconstruction of other data or images, including CT, MR, and PET data or images.

In some aspects, the controller 110 may perform an image registration between various generated or accessed maps and images. In addition, the controller 110 may be configured to analyze the generated images, for example, to obtain a variety of information about the regions of interest, such as target or critical structures, including their locations, density, stopping power, acoustic properties, such as sound speed, and so on. For example, the controller 110 may identify strong acoustic absorbers, reflectors, and other anomalies. These may then be used to select the most reliable primary measurements for triangulation, for example. Such analysis may be performed offline, or online in substantially real-time. In some aspects, the controller 110, upon analyzing the sonic signals, may make a determination that receivers are improperly positioned, or data acquired is insufficient or inadequate. To this end, an indication or notification may be provided to a user, for instance, to halt operation, to reposition receivers, and so on.

The controller 110 may also be configured to generate a report. The report may have any form and include various information. In one non-limiting example, the report may visually identify an estimated end range of a selected radiation beam overlaid on an image, such as an ultrasound image. The report may also indicate an estimated end range relative to a planned location or a planning target, or planning target volume. The report may also be in the form of a visual or audio alert, for instance, in the case that an estimated end range is outside of a predetermined threshold value. The report may also include instructions or signals for adapting a treatment plan, or for controlling the delivery system 104, positioning system 106 and imaging system 108.

Although the delivery system 104, positioning system 106, imaging system 108 and controller 110 are illustrated in FIG. 1 as different systems, in some implementations, any or all of these could be combined into one integrated system. For example, the delivery system 104 and imaging system 108 may be combined to share the same coordinate system, allowing images to be acquired during treatment, without need for moving the patient. Such integrated system would also be advantageous in minimizing the time interval between treatment and imaging. In another example, the controller 110 and imaging system 108 could be combined. Furthermore, analysis, processing and other steps may be carried out exclusively or shared between processors or processing units belonging to the controller 110, imaging system 108, positioning system 106, delivery system 104. In some implementations, the controller 110 or an integrated system that includes the controller 110 may be specifically designed, configured or programmed, for example via software, firmware or hardwired instructions, to carry out algorithms and methods described herein, including steps for estimating the end range of a radiation beam. As such, the controller 110 or system may not be considered to be a generic computer, but rather an application-specific system in accordance with aspects of the present disclosure.

Figure 2:
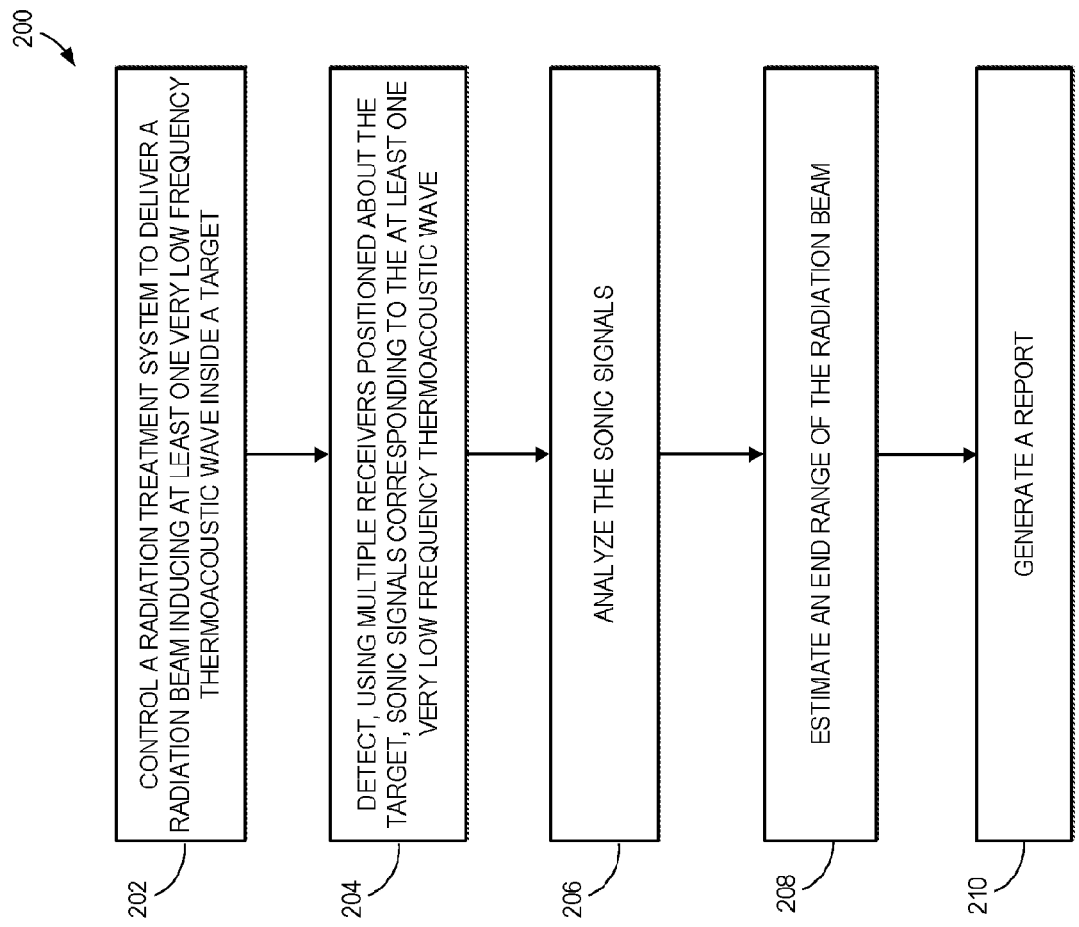
FIG. 2 is a flowchart setting forth steps of a process in accordance with aspects of the present disclosure.

Referring now to FIG. 2, steps of a process 200 in accordance with aspects of the present disclosure are described. The process 200 may be carried out by a variety of suitable systems, including systems described in the present disclosure. In some implementations, the process 200 may be embodied as a program, firmware, software or instructions stored in a memory, such as a non-transitory computer readable medium or other data storage, and executable by one or more processors.

The process may begin at process block 202 with controlling a radiation treatment system to deliver one or more radiation beams inducing at least one low frequency thermoacoustic wave inside a target. This may include providing a scout radiation beam or a field of a treatment plan. Then, at process block 204, sonic signals corresponding to the induced low frequency thermoacoustic wave(s) may be detected using multiple receivers positioned about the target. As described, this may include detecting signals in a frequency range approximately between DC and 300 kHz, although other values may be possible.

The sonic signals may then be analyzed and an estimate of an end range of the radiation beam may be obtained, as indicated by process blocks 206 and 208. In some aspects, the sonic signals may be analyzed to determine time-of-flight information associated with induced low frequency thermoacoustic wave(s). Such time-of-flight information may include absolute time-of-flight values from the source position to different receivers, as well as relative time shifts or differences between the various times-of-flight. A triangulation technique may then be utilized to estimate the end range.

In some aspects, a two-step process may be performed to estimate the end range at process block 208. As described, a preliminary estimate may be first obtained by applying a beamforming technique, such as a one-way beamforming. The preliminary estimate may then be refined or corrected, based on estimates obtained using the time-of-flight information or comparisons measured signals to a reference or database, to generate a corrected estimate of the end range. To this end, both analyzed sonic signals and a priori information including beam, properties/trajectory and thermoacoustic emissions may be utilized at process block 208.

A report may then be generated at process block 210. The report may be in any form and include any information, such as various maps, images, end range estimates and so on. The report may be provided to a user, clinician, or relayed to a treatment planning system or workstation. In some implementations, the report may be in the form of an audio or visual alarm or indication informing, for example, when a treatment or treatment conditions are determined to be unsafe, or whether an estimated end range exceeds a pre-determined threshold value. The report may also be in the form of signals or instructions for controlling or adapting a treatment delivery. To this end, the signals or instructions may be sent to a delivery system or positioning system to halt a treatment or reposition a patient, or both, for example. The report may include other actions to be executed at process block 210.

Figure 3:
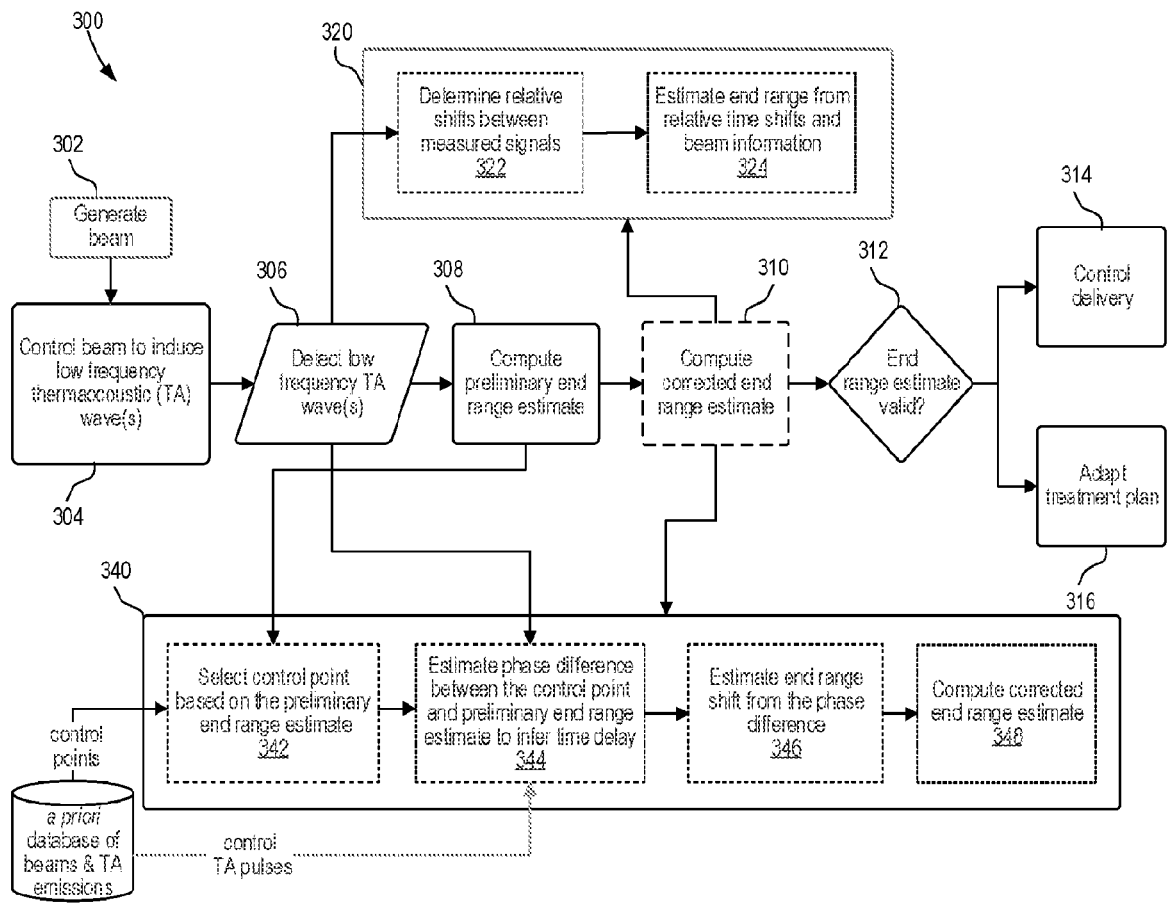
FIG. 3 is another a flowchart setting forth steps of a process in accordance with aspects of the present disclosure.

Turning to FIG. 3 a flowchart setting forth steps of a process 300 in accordance with aspects of the present disclosure is shown. The process 300 may be carried out by a variety of suitable systems, including systems described in the present disclosure. In some implementations, the process 300 may be embodied as a program, firmware, software or instructions stored in a memory, such as a non-transitory computer readable medium or other data storage, and executable by one or more processors.

The process 300 may begin at process block 302 with generating one or more radiation beams. At process block 304, the generated beam(s) may be controlled to induce one or more low frequency thermoacoustic waves. For example, a generated beam may be chopped to generate a pulsed beam. The low frequency thermoacoustic waves are then detected, as indicated by process block 306, by measuring sonic signals using various receivers positioned about a target or patient. A preliminary end range estimate may then be computed at process block 308. For example, a one-way beamforming technique may be applied to the sonic signals measured to compute the preliminary end range estimate. In some implementations, a corrected end range estimate may then be computed at process block 310, for instance, based upon time-of-flight information and a priori information, such as beam information (trajectory, diameter, and energy) and simulated emissions information. Based upon the preliminary and/or corrected end range estimates, a determination may be made at decision block 312 whether the estimates are valid or fall with acceptable limits. Treatment delivery may then be controlled or a treatment plan adapted, or both, as indicated by process blocks 314 and 316, respectively. For instance, the treatment plan may adapted in substantially real time, or online, as well as offline for a future treatment.

Process blocks 320 and 340 represent different correction schemes for improving upon the preliminary end range estimate computed at process block 308. These may be carried out independently, or sequentially. In particular, process block 320 may be carried out, for example, when a database of simulated thermoacoustic emissions corresponding to known beam trajectories and ranges is unavailable. As indicated by process block 322, sonic signals detected at process block 306 can be analyzed and correlated to determine relative shifts or time-of-flight differences of induced thermoacoustic waves between the various receivers. For example, a triangulation technique may be utilized. In addition, a priori information, such as beam information, can be utilized at process block 324.

Process block 340 may be carried out when a database of simulated thermoacoustic emissions corresponding to known beam trajectories and ranges is available, as shown in FIG. 3. As indicated at process block 342, the preliminary end range estimate may be used to select a control point. The control point may be selected to be nearest to the preliminary end range estimate. Control points representing end ranges of beams with known parameters, such as beam energy, orientation, diameter in air at isocenter, and so on, may be obtained by simulating various beams under different conditions, for example, using Monte Carlo techniques. From the simulated dose map thermoacoustic emissions corresponding to the control beam and control point may be simulated. Then, at process block 344, a phase difference associated with the control point and the preliminary end range estimate may be determined. To do so, judicious filtering and the Fourier-shift theorem may be applied at process block 344. From the phase difference, a time delay or time-of-flight difference between the measurement, or preliminary end range estimate, and simulation, or control point, may be inferred. Using the time delay, an end range shift may be estimated at process block 346, respectively. Process blocks 342-346 may be repeated using sonic signal data from multiple receivers. Then, at process block 348, the end range shifts, corresponding to multiple sonic receivers, may be used to compute the corrected end range estimate, for example, via a least-squares approach. In some aspects, a priori information may be applied at process block 348 to further improve the corrected end range estimate.

Figure 4:
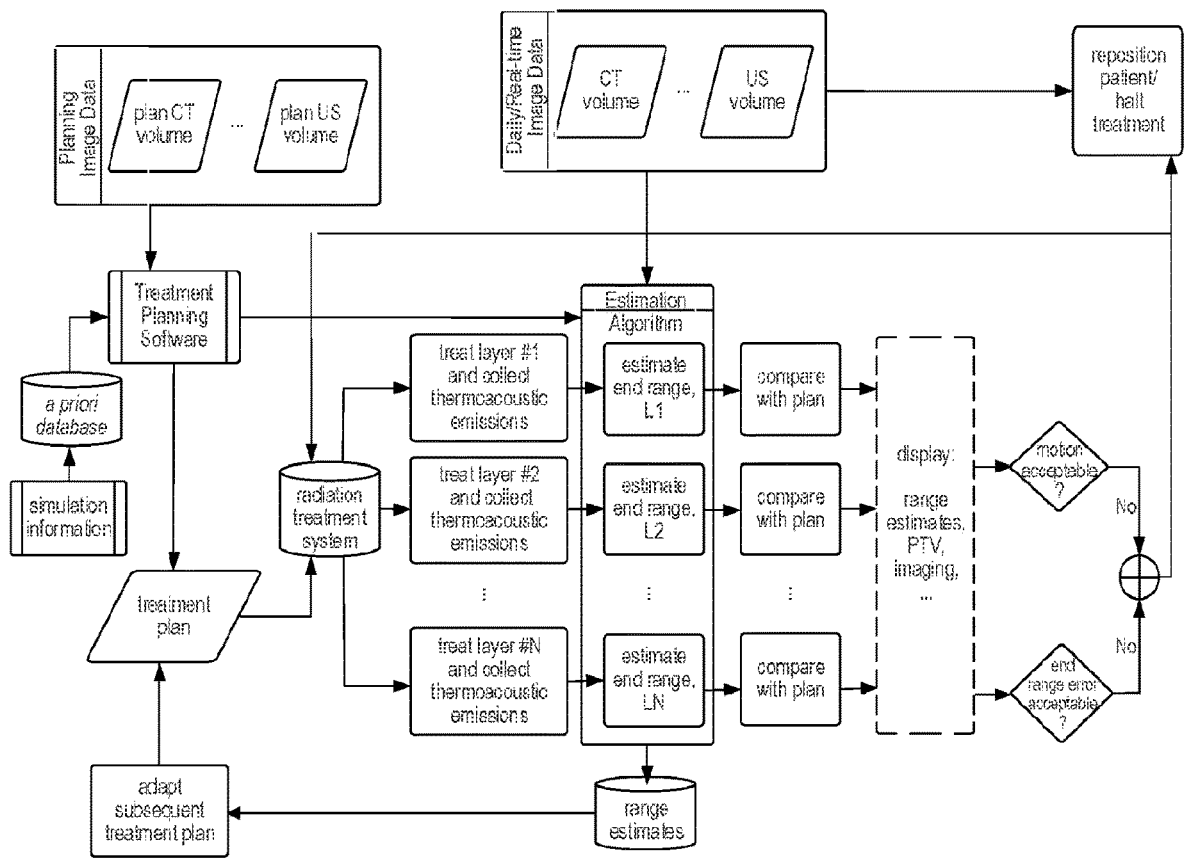
FIG. 4 is yet another a flowchart setting forth steps of a process in accordance with aspects of the present disclosure.

Referring now to FIG. 4, another process 400, in accordance with aspects of the present disclosure is illustrated. As shown, the process 400 may begin with a planning stage in which planning image data, including CT, ultrasound and other imaging data, are utilized, along with a priori information, by a treatment planning software to generate a treatment plan. The treatment plan may then be delivered by a radiation treatment system, as described with reference to FIG. 1, for example. The treatment plan may include multiple treatment layers, indicated as #1, #2, . . . #N in the figure. Each treatment layer may include one or more treatment fields, and/or one or more scout beams. As shown, thermoacoustic emission or sonic signal data may be collected, for instance, using a sonic system. An estimation algorithm may then be executed to obtain an end range estimated for each treated layer. The estimation algorithm may utilize daily (prior to treatment) and/or real-time imaging data, as shown. Computed end range estimates may also be stored in a database, and utilized to adapt a subsequent treatment plan, for example, when another fraction is being delivered.

The estimates may be compared with a treatment plan, and optionally displayed, for example, overlaid on various images. Other information may also be displayed, including target positions, planning target volumes, and so on. The estimates may then be utilized to determine a motion or a range error. Based on whether such motion or error is found acceptable, for example, compared to predetermined threshold values, a patient may be repositioned or treatment is halted.

Figure 5:
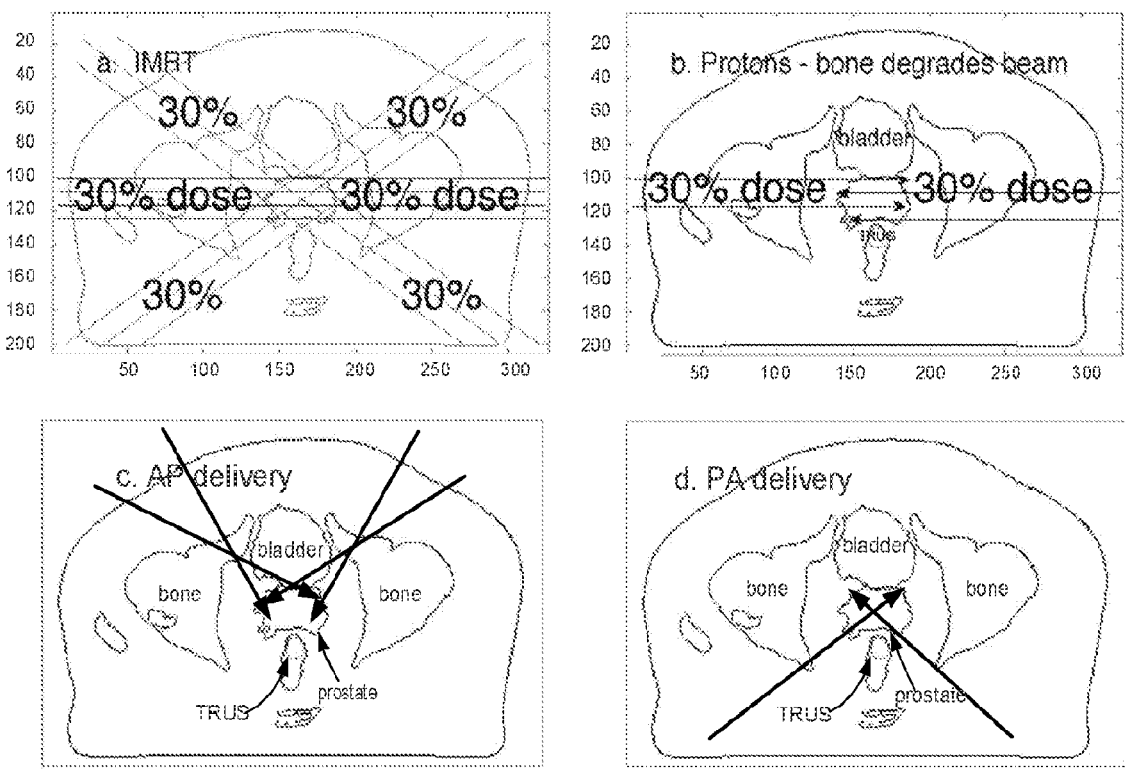
FIG. 5 are example images illustrating treatment of a prostate using (a) IMRT and (b) proton therapy and a possible "blue sky" techniques envisioned (c) and (d) in accordance with aspects of the present disclosure.

One controversial application of ion therapy is prostate cancer treatment. To spare radiosensitive rectal tissue the standard prostate cancer protocol treats only with horizontal beams, which travel through thick bony structures before reaching the prostate. Bone degrades the proton beam's energy spectrum, minimizing the advantage of ion therapy over intensity modulated x-ray radiation therapy (IMRT). Although IMRT delivers 30% of the therapeutic dose to larger regions of the bladder and rectum (FIG. 5 (*a*)) as compared to ion therapy, horizontal delivery maximizes proton pathlength through hip and thigh bones, as appreciated from FIG. 5 (*b*). A "blue-sky" two-step protocol envisioned in FIGS. 5 (*c*) and (*d*) can minimize the ion path through bone and spares both bladder and rectum. This protocol, however, is sensitive to range errors, because overshooting during anterior-posterior (AP) delivery in FIG. 5 (*c*) unnecessarily exposes the rectum, and overshooting during posterior-anterior (PA) delivery in FIG. 5 (*d*) exposes the bladder. This is just one high-level treatment example that would benefit from the present approach of thermoacoustic range verification.

The above-described systems and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain arrangements and configurations applied to range verification for ion therapy are presented, although it may be understood that other configurations may be possible, and still considered to be well within the scope of the present invention. Likewise, specific process parameters and methods are recited that may be altered or varied based on variables.

EXAMPLE

Range verification via thermoacoustic detection of the Bragg peak is a natural consequence of the conversion of deposited dose to mechanical pressure pulses. Treatment plans are quantified in terms of Grays, 1 Gy=1 J/kg, whereas acoustic pulse amplitudes are quantified by Pascals, 1 Pa=1 $N/m^2$=1 $J/m^3$. The units for dose and pressure differ only by a multiplicative factor of target density, $\rho$. The dimensionless Grüneisen ($\Gamma$) is simply the constant of proportionality between energy density and thermally induced pressure change. Assuming rapid dose deposition, $\delta p = \Gamma \rho D$, where D is the dose delivered and $\delta p$ is the pressure change induced by applied dose. In soft tissue, $\Gamma \sim 0.1$ and $\rho \sim 1000$ $kg/m^3$ so instantaneous delivery of 2 Gy increases pressure by 200 Pa at the Bragg peak. Delivery of 1 cGy, however, generates only 1 Pa. Pressure amplitude at remote transducer locations is lower, primarily due to radial decay. Even under ideal conditions thermoacoustic range verification will require detecting weak pressure pulses.

Thermoacoustic range verification shares some similarities with thermoacoustic imaging, but differs in important ways. Both range verification and imaging require sufficiently fast dose deposition satisfying stress confinement to ensure that ion delivery builds up pressure faster than it can propagate away. Assuming lateral coordinates of the ion beam line are known, thermoacoustic range verification requires recovering only the Bragg peak location along the beam line. Recovering only one number, rather than an $N^3$ volume of voxel values relaxes the standard imaging requirements for high-resolution and artifact-free data reconstruction.

Fundamental challenges to thermoacoustic range verification are the therapeutic dose limit, which in turn limits induced pressure amplitude and severe bandlimitation caused by ion-range straggling. Unlike photoacoustic imaging, the aim of ion therapy is to deposit ionizing dose, so signal averaging is fundamentally limited by the fractionated dose. Longitudinal and lateral ion straggle smooth the thermoacoustic source and bandlimit signals detected at distal and lateral transducer locations, respectively. Bandlimitations from "straggle" caused by ion scattering are highlighted in the example of FIG. 6, which shows the Bragg curve and ion tracks in waterbath using default mode with identical initial conditions, $FWHM_p=0$. For clarity of display only 99 ions were tracked. Specifically, FIG. 6 (*a*) shows that 230 MeV protons travel $z_{230} \pm \sigma z_{230} = 325 \pm 3.6$ mm, $\sigma_{1230}=7.7$ mm, FIG. 6 (*b*) shows the magnification of distal portion of 230 MeV beam, and FIG. 6 (*c*) shows that 49 MeV ion travel $z_{49} \pm \sigma_{z49} = 21.1 \pm 0.4$ mm, with final lateral distribution $\sigma_{149}=0.52$ mm. To highlight lateral straggle, FIGS. 6 (*b*) and (*c*) are displayed on the same spatial scale.

In some aspects, hybrid B-mode/thermoacoustic ultrasound probes enable range estimate overlays that are inherently robust to soundspeed inhomogeneity because ultrasound images created by 2-way beamforming can suffer the same errors as beamformed range estimates. Ultrasound images may be distorted by soundspeed variations. Beamformed range estimates can be similarly distorted, and therefore very accurate relative to underlying tissue morphology.

Figure 7:
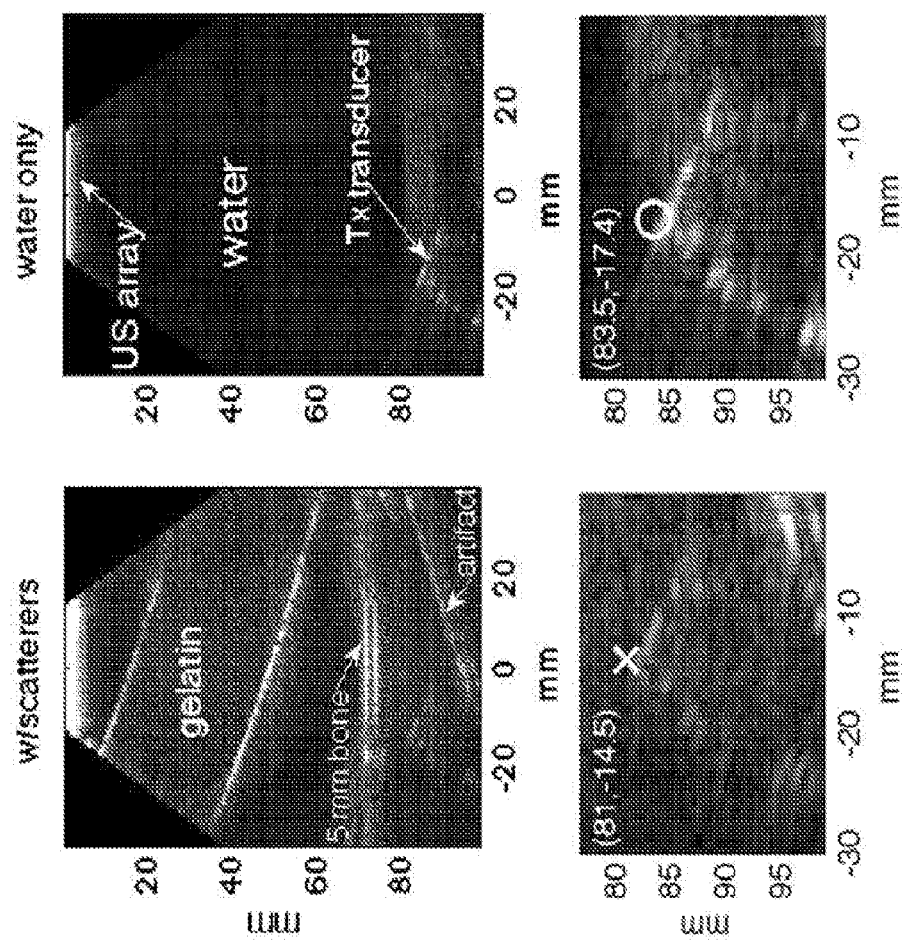
FIG. 7 are example B-mode ultrasound images, in accordance with aspects of the present disclosure.

FIG. 7 highlights this phenomenon by showing results obtained using a pitch-catch acoustics setup in which a single element transducer was utilized as an acoustic source to simulate a Bragg peak. Pulses were received by a P4-1 ultrasound imaging array, which generated B-mode images immediately prior to each pitch-catch experiment. Pulses propagated from single element transducer through room temperature water in the control experiment; a tissue mimicking gelatin block and 5 mm bone sample were placed between transducers. One-way beamforming was used to estimate the position of the acoustic source. In each case, the beamformed image achieved its maximum on the corner of the single element transducer closest to the imaging array. Acoustic inhomogeneity shifted the image of the single element transducer so that its corner moved from (83.5 mm, −17.4 mm)=(depth,lateral) coordinates to (81 mm, −14.5 mm). As illustrated, beamformed thermoacoustic range estimates are inherently co-registered to ultrasound images when the thermoacoustic and pulse-echo imaging flight paths coincide.

Figure 6:
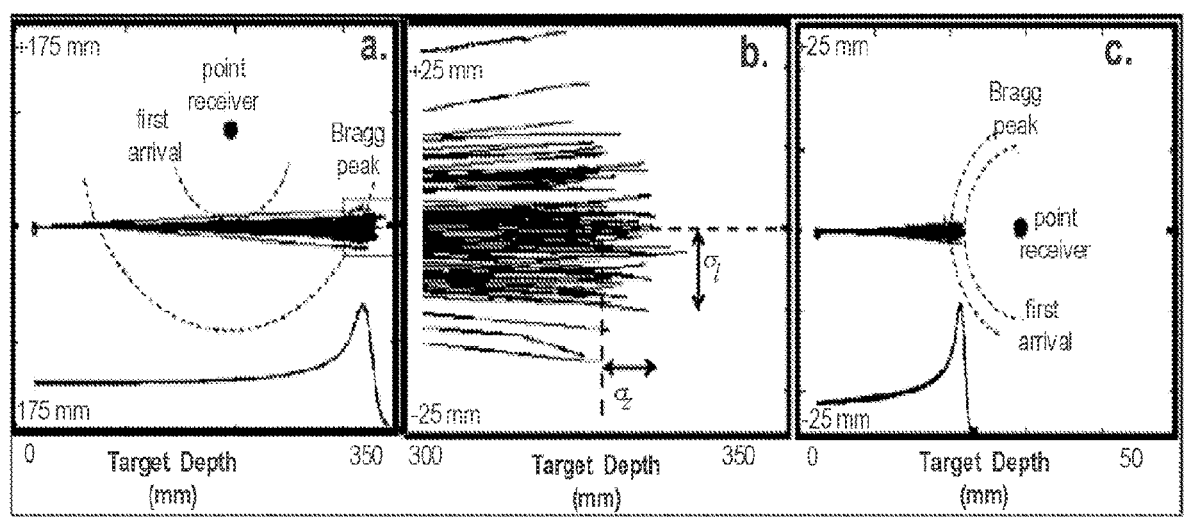
FIG. 6 are example images illustrating the Bragg curve and tracks of a proton beam in water bath.

Transducer locations along a beamline and distal to the Bragg peak may be advantageous for range verification. At proximal transducer locations laterally offset from the beamline, emissions from the beamline are summed with emissions from the Bragg peak and confound range verification, as seen in FIG. 6 (a). Measurements were obtained from distal transducer locations using a low-energy beamline at a national laboratory. Numerical simulations for high-energy pencil beams delivered with lateral and oblique gantry angles were also been studied.

Figure 8:
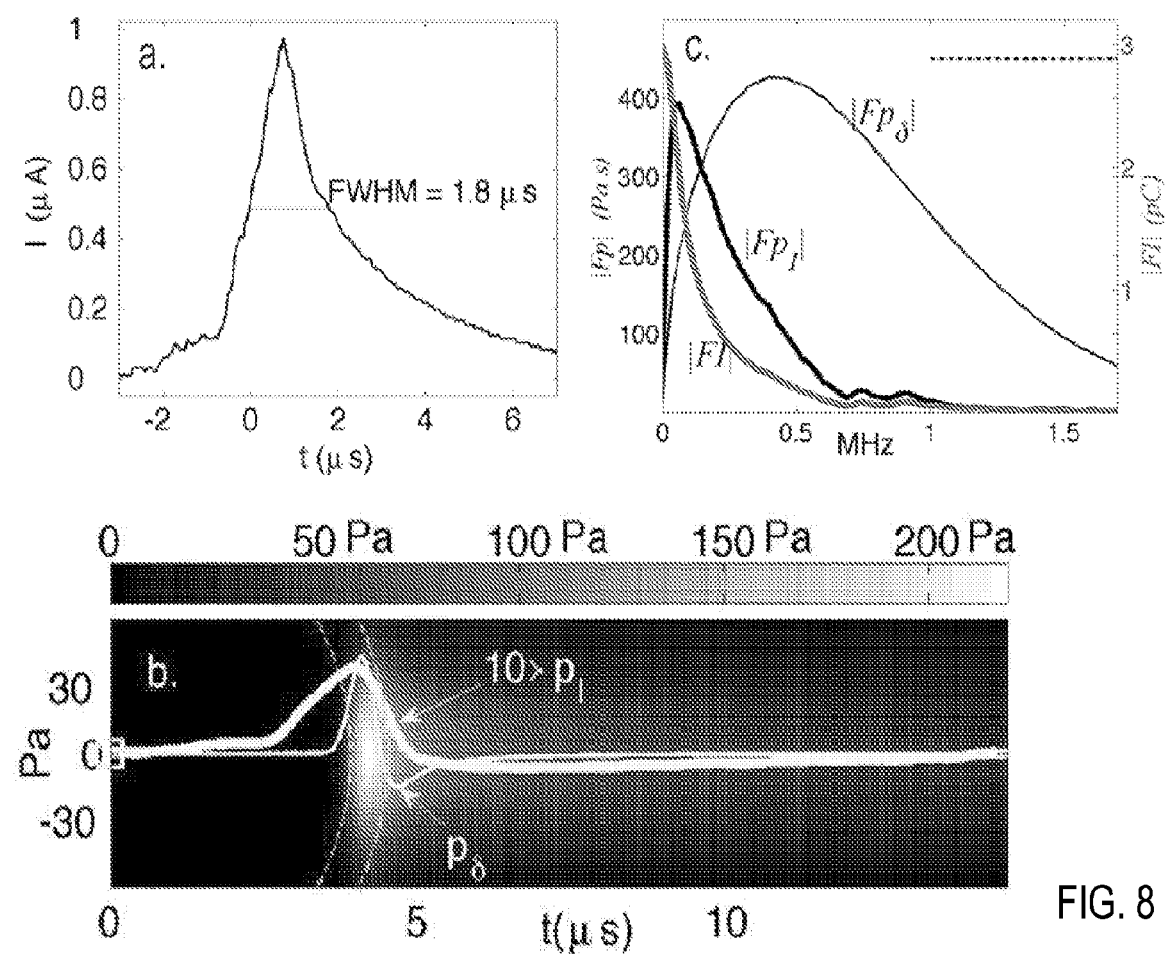
FIG. 8 is a graphical illustration of 50 MeV protons incident upon a water bath indicating (a) measured envelope of delivered proton current, I, (b) modeled initial pressure due to instantaneous and experimental spills and (c) spectra and the transducer's sensitivity band.

As an example, FIG. 8 shows pulses due to 50 MeV ions in a waterbath. Specifically, FIG. 8 (a) shows the measured envelope of delivered ion current, I. FIG. 8 (b) shows the initial pressure due to instantaneous spill modeled in the gray scale image. Dashed green lines represent spherical integration surfaces. Thermoacoustic emissions arriving at the distal location indicated by a square yellow box are plotted in yellow. Emissions from instantaneous ($p_\delta$) and experimental ($p_I$) spills are plotted in thin and thick yellow lines, respectively. FIG. 8 (c) shows spectra and the transducer's sensitivity band. |FI|, the magnitude of the current spectrum is plotted in thick grey, whereas spectra of thermoacoustic emissions bandlimited by I are plotted in thick black. Idealized pulses due to instantaneous delivery are plotted with thin lines. The ideal spectrum generated by the Bragg peak, $Fp_\delta^{peak}$ achieved its maximum below approximately 500 kHz with full-width at half-maximum of 1 MHz. 50 MeV ions penetrate only 2 cm into water and soft tissue and therefore experience less "straggle" than higher energy ions, which undergo more scattering as they travel deeper into tissue. Longitudinal and lateral spreading of the ion beam reduces bandwidth of thermoacoustic emissions and is important to model accurately. Bandwidths of experimentally realized pulses were reduced to 700 kHz, as indicated by the thick lines in FIG. 8 (b).

Using a P4-1 ultrasound imaging array, thermoacoustic range verification was implemented in a waterbath and gelatin phantom, with a gap filled alternately by oil and air. A shift in the range of about 3 cm was detected when the air gap was filled with oil, but thermoacoustic estimates of the range agreed within 1 mm to Monte Carlo simulations as detailed in Table 1. In phantom experiments, Bragg peak locations were overlaid in color on greyscale ultrasound images providing perfect co-registration to underlying morphology. Since clinical ultrasound transducer sensitivity band was mismatched to the spectrum of thermoacoustic emissions, signal averaging was performed and cumulative dose applied to the phantom exceeded 2 Gy at the Bragg peak. An injection line "chopper" deflected the beam as it passed between parallel plates, allowing ions to pass to the cyclotron only when the plates were discharged. Ion pulses with peak current of 2 μA delivered 4 pC in 2 μs.

TABLE 1

| Range Estimates in Water | | |
| --- | --- | --- |
| 1 cm left | centered | 1 cm right |
| 21.7 ± 0.2 | 21.9 ± 0.0 | 22.0 ± 0.02 |

Thermoacoustic emissions were measured by a programmable ultrasound system (Verasonics V1) with a 96-channel P4-1 cardiac array, and also by a single element fishfinder (Garmin 010-10272-10). The V1 system electronics sampled signals at 30 MHz that were then amplified by 43.5 dB. The transducer element in the fishfinder had a diameter 44 mm. In addition, the tranducer element was modified with a BNC connector and impedance matching, amplified by 60 dB using a low noise preamplifier (Olympus 5660B) and read out to an oscilloscope (Tektronix TDS7104) at a sampling rate of 80 ns. Marketing specifications for the transducers' sensitivity bands are 1-4 MHz and 50-200 kHz respectively.

To analyze the impact of the ion pulse duration, thermoacoustic emissions were evaluated two ways, assuming impulsive delivery and the measured current, I(t). In addition, for the sake of comparison, an evaluation was made at the transducer location, 6.5 mm distal to the Bragg peak on the beamline. Thermoacoustic emissions due to idealized instantaneous, $p_\delta$, and experimentally realized, $p_I$, spills were modeled, shown in FIG. 8 (b) by thin and thick yellow lines, respectively. Dashed green lines represent spherical surfaces over which the non-negative source term, Γd, is integrated to compute pressure. Although initial pressures exceeded 200 Pa in the Bragg peak, $p_\delta(x, t)$ remained below 50 Pa at the distal transducer location, namely x=(0,0,6.5 mm) as the thermoacoustic pulse traveled past. The experimentally realized pressure, $p_I(x, t)$, was reduced by approximately one order of magnitude, due to convolution by the delivered current envelope, I(t). $p_I$ is compared to $p_\delta$ in FIG. 8 (b).

Figure 9:
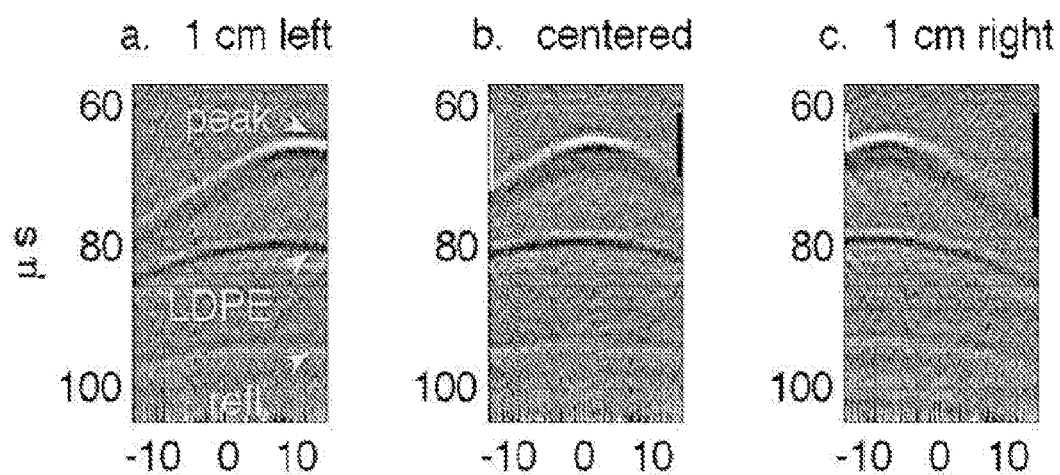
FIG. 9 are example ultrasound images indicating reconstructions of sonic signals that reveal the Bragg peak as a monopole, in accordance with aspects of the present disclosure.
Figure 9:
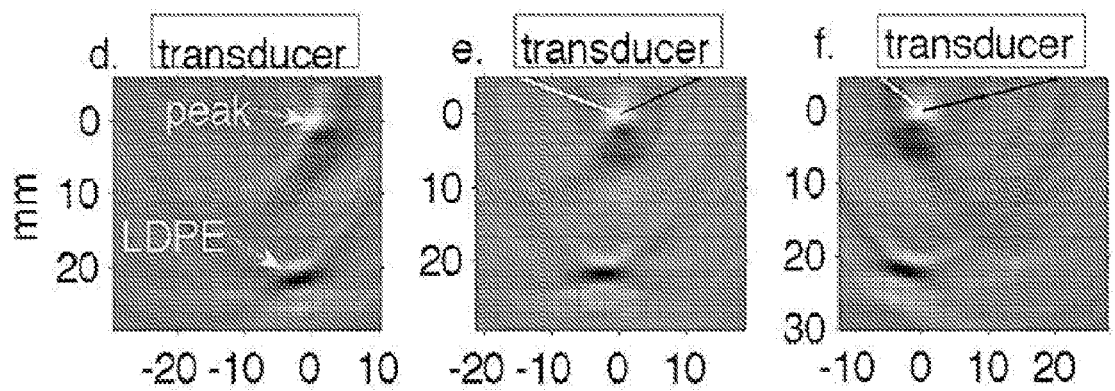

Results in the water tank indicate that the pulse emanating from the Bragg peak traveled outward in all directions. The portion of the pulse that traveled towards the sidewall was reflected and returned to the transducer array. All three pulses, Bragg peak direct, LDPE sidewall and Bragg peak reflected, can be seen in FIG. 9 (a)-(f), where readouts from all 96 transducer channels are displayed. Data was collected at three transducer positions approximately 1" from the tank wall. The shift in the arcs corresponds to a 1 cm lateral translation between measurements. One-way beamforming was applied, and the Bragg peak was reconstructed as a round monopole, in FIGS. 9 (a)-(f). The tank wall appears as an oblong structure in the figures. Measuring the distance between the peak value in the monopole and centermost zero crossing in the bipolar LDPE consistently overestimated the 21.1 mm range as appreciated from FIGS. 9 (d)-(f) and Table 1.

Phantoms were also fabricated to produce "U-shaped" cavity designed to mimic an intestine located at the end of a 135 mm long styrofoam cone. The cavity had ellipsoidal cross-section (26 and 36 mm primary axes). The ion beam traveled through the Styrofoam cone and the cavity before entering TM material. Range estimation was performed with the cavity both empty and full of olive oil. When full, the beam stopped midway through the olive oil, indicated by the solid arrow in FIG. 10 (d). When empty, the beam traveled through the air-filled cavity before stopping in the TM phantom, as indicated by the dashed arrow in the figure.

Figure 10:
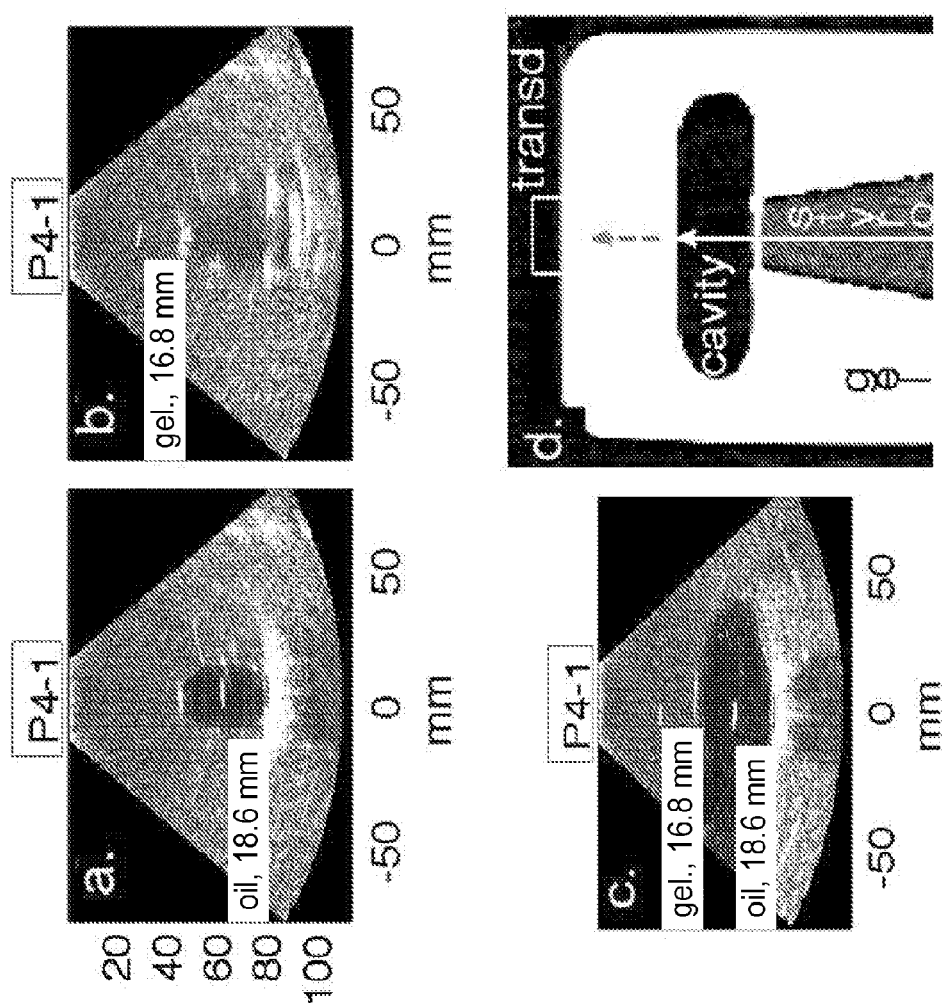
FIG. 10 are example overlays (a)-(d) onto grayscale ultrasound images indicating an identified Bragg peak in a phantom having a Styrofoam cone and cavity, in accordance with the aspects of the present disclosure; (d) is a CT image of coronal slice of the phantom.

Data was again collected with transducers located on the beamline, distal to the Bragg peak, as shown in FIGS. 10 (a)-(c). B-mode imaging was performed first to ensure the P4-1 transducer was located along the beamline, and raw data was saved to disk in order to have B-modes perfectly co-registered with thermoacoustic estimates. Without moving the P4-1 array, 1024 thermoacoustic pulses were averaged on the Verasonics' host computer and saved to disk. Thermoacoustic pulses were bandpass filtered and backprojected using 1540 m/s as a measure for sound speed. A threshold was applied to select the Bragg peak, which was overlaid in yellow onto the corresponding B-mode image. It was again confirmed that the low frequency fishfinder provided better SNR with fewer signal averages than the P4-1 array. Improved sensitivity of the low frequency—and inexpensive—fishfinder supports the importance of dedicating low frequency elements to thermoacoustic range verification.

A comparison of the sagittal images shown in FIGS. 10 (a) and (b) indicates translation of the Bragg peak due to air in the intestinal cavity. Additionally, it highlights the difficulty of using ultrasound imaging alone for range verification. The oil-filled cavity in FIG. 10 (a) appears as an anechoic dark region, but reflection of ultrasound at an air/tissue interface in FIG. 10 (b) makes the speckle pattern inside the cavity very nearly that of the surrounding phantom material. Locations of the Bragg peaks from both empty and oil-filled measurements are overlaid onto the oil-filled coronal ultrasound image in FIG. 10 (c). The beam traveled about 10% further in olive oil than in the phantom, consistent with the 10% density difference between olive oil and gelatin phantom material.

Figure 11:
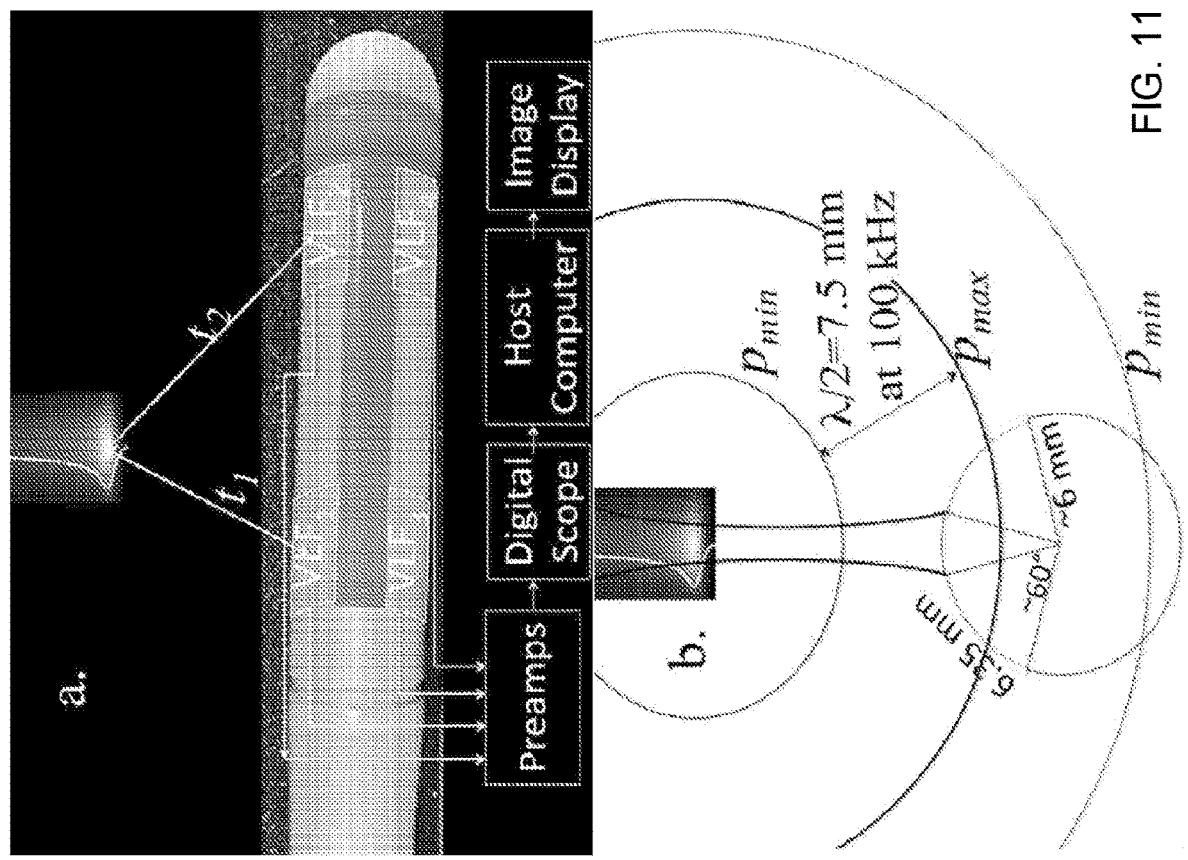
FIG. 11 shows a (a) perspective view and a (b) cross-sectional view of a biplane TRUS array having multiple low frequency element locations.

As described, in some implementations, sonic signals may be compared or correlated to obtain estimates of an end range of a radiation beam. By way of example, FIG. 11 shows one non-limiting implementation illustrating a Biplane TRUS array with four low frequency elements. A priori information about the target and beam parameters and redundant information from all four low frequency elements can be used to overcome the classic half-wavelength resolution limit. Time-of-flight (TOF) estimates from low frequency signals alone might not be accurate, however, differences in TOF can be found accurately. Cross-correlating signals from all four low frequency elements yields three independent time delays, and leaves only one unknown. For the purposes of illustration, let $t_1$ represent unknown TOF for element #1, $\delta t_k$ represent the time delay between elements #1 and #k, for k=2, 3, 4. Consider the element orientation in FIG. 10, and treat the Bragg peak as a point source. Determining the Bragg peak location in 3-space requires TOF for three elements, but three time delays are known, each of which is a function of the unknown $t_1$. For any pair of elements and TOF $t_1$ the Bragg peak must lie on the intersection of spheres of radii $t_1$ and $t_1+\delta t_k$ centered at elements #1 and #k, respectively.

Figure 12:
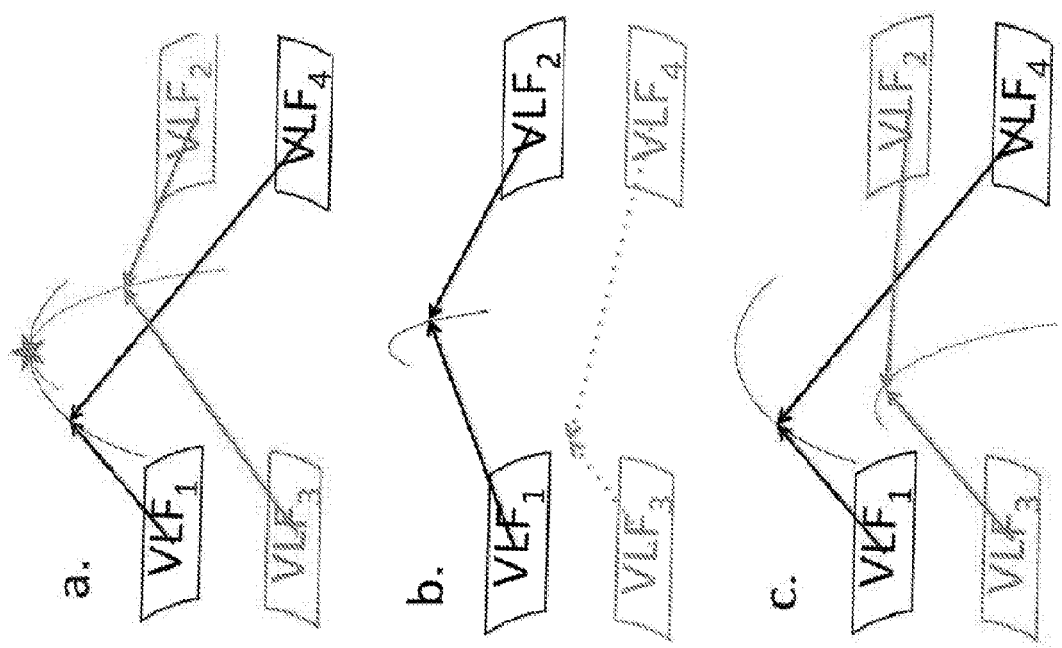
FIG. 12 is an illustration of a triangulation technique, in accordance with aspects of the present disclosure.

A triangulation technique is illustrated in FIG. 12. Ideally, all four spheres intersect in a single point for the correct choice of $t_1$ as shown in FIG. 12 (a). The family of circles is determined by varying $t_1$ and the intersection of spheres centered at elements #1 and #4 as shown in black. The same can be done for red elements #2 and #3. For the true value of $t_1$ these circles should intersect at the Bragg peak, indicated by a star.

As discussed, information about the distal edges of all strong scatterers as imaged by an ultrasound imaging array as well as a priori information about the ion beam may be utilized. Such information may be tabulated and compared to range estimates & Monte Carlo estimates to quantify accuracy. In some aspects, systematic errors due to repeatable system failures and features such as time lags in electronics and transit time through transducer element may be addressed. For instance, repeatable errors can be corrected in software to tighten range estimates, with the goal of delivering results with random errors.

The above triangulation approach may fail when the problem happens to be underdetermined due to symmetry or overdetermined due to noise (FIGS. 12 (b) and (c)). Noisy data may result in curves that never intersect. However, such curves are likely close so that a $t_1$ may be selected to minimize the distance between the curves. In the unlikely situation that the ion beam is positioned symmetrically with respect to the low frequency elements, all time delays are zero, $\delta t_k$=0, and the Bragg peak must lie somewhere on the vertical line centered between all four elements. In this case, measured signals may be cross-correlated to modeled thermoacoustic emissions assuming in a water target, the known beam energy, current, I(t), and beam FWHM. When the Bragg peak is significantly out of plane, two elements may not detect significant signal and a failsafe may ask the user to reposition the probe. It may be noted that seeking the intersection of arcs corresponding to diagonally paired transducer elements, as described, is merely an intuitive example. It may be readily appreciated that a variety of other numerical methods could be applied to estimate the true time-of-flight.

Figure 13:
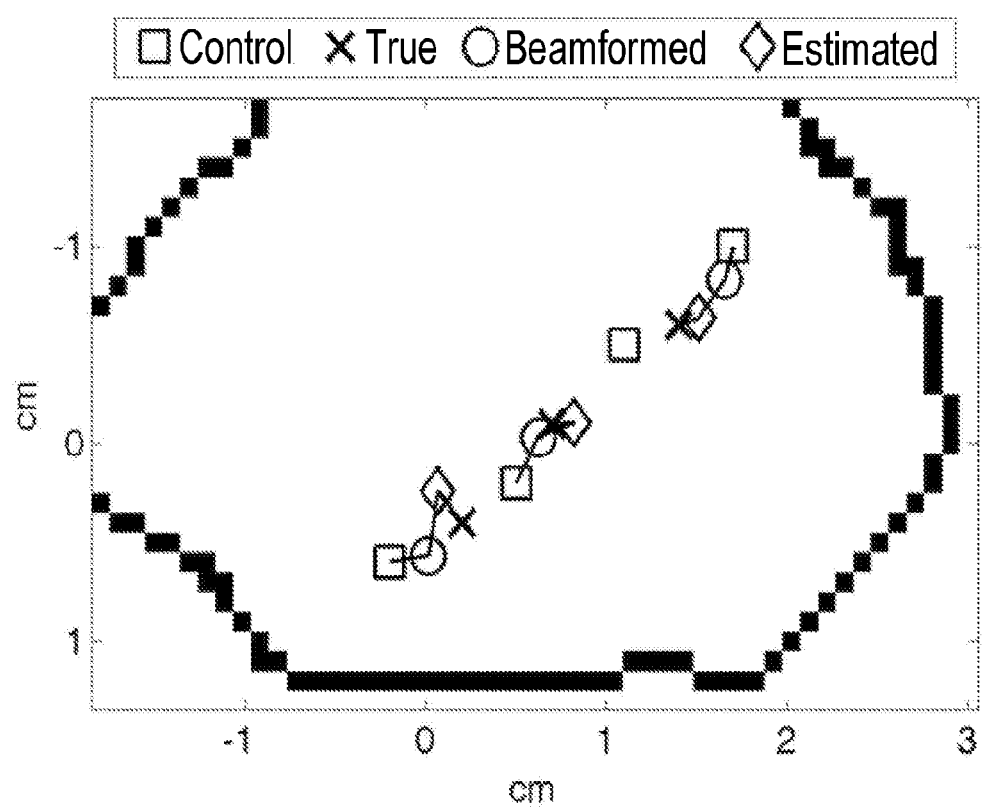
FIG. 13 is a CT image indicating estimate end ranges, in accordance with aspects of the present disclosure.

Computing accurate range estimates from low frequency data by comparison to a database of simulated beams and corresponding thermoacoustic emissions was performed as follows. Energies of an oblique beam were altered deliberately in increments of 5 mm water equivalent thickness (WET) to simulate scenarios of under- or overshoot of protons that might occur during treatment. For each of seven beam ranges, thermoacoustic emissions were simulated and white noise was added to test robustness of the method. Offline estimates were obtained from noisy data for oblique beams #3, 5, and 7, referred to as "measured" data. Noise-free data and true Bragg peak locations for neighboring beams #2, 4, 6, and 8 were taken to be a priori control data. True Bragg peak locations are depicted by squares in FIG. 13. For each set of measured data, the beamformed range estimate was computed and the nearest control location was selected for use in updating the beamformed range estimate.

For each thermoacoustic receiver transducer element, a time-of-flight to the Bragg peak was estimated from time-of-flight differences between emissions from the measured and control beams and a priori knowledge of time-of-flight from transducer to the Bragg peak of the control beam. Measured and control signals were nulled for all time after onset of rarefaction to emphasize the initial thermoacoustic pressure increase used to compute time-of-flight. The Fourier shift theorem was applied to estimate time shifts between the noisy and control emissions by fitting a straight line to phase shifts in the lowest frequency Fourier components. Comparing two time series with hundreds of points robustly yielded a single estimate for the time shift between them. Assuming a constant sound speed, the known times-of-flight between transducers and the control Bragg peak location were updated with time shifts, to estimate times of flight to the unknown Bragg peak location.

Specifically, if a thermoacoustic source is considered as a single point then a triangulation needs only three transducer locations and times of flight, $t_k$, to localize the Bragg peak at $x=(x, y, z)$ by solving for each transducer location $x_k=(x_k,y_k,z_k)$ $$|x-x_k|^2=(v_s t_k)^2 \text{ for } k=1,2,3,\ldots N \qquad (1)$$

where $v_s$ represents soundspeed and N is the number of transducer locations.

In one simulation study, four transducer locations were used. A least-squares computation approach was implemented by first linearizing the system of equations. Subtracting for $j \neq k$ yielded $6=N(N-1)/2$ linear equations, $$2x \cdot (x_k-x_j)=(|x_k|^2-|x_j|^2)-v_s(t_k^2-t_j^2) \qquad (2)$$

With all parameters known, except for the desired Bragg peak location, a least squares solution, $x_{LSQ}$, may be found.

For arbitrary transducer locations the least squares solution is unique. However, co-planar transducer locations led to a rank-deficient system. The least-squares solution may be orthogonal to the transducer plane, i.e., $x=x_{LSQ}+cn$, with $n=(0,0,1)$ the unit normal to the coronal transducer plane. The normal component may then be determined by returning to the original nonlinear equations $$|x_{LSQ}+cn-x_k|^2=(v_s t_k)^2 \qquad (3)$$

and expanding to get k quadratic equations with respect to c, $$c^2+2n \cdot x_k c+[|x_{LSQ}-x_k|^2-(v_s t_k)^2]=0 \qquad (4)$$

The quadratic formula yields two solutions, $c_{k\pm}$, to each equation. For the above transducer geometry, least-squares solutions were in the coronal plane located 28 mm posterior, so desired solutions were given by elevating the least squares solution by $c_{k+}$. If the Bragg peak were truly a point source and the computations were error free, then the $\{c_{k+}\}$ would be identical for noise-free simulations. In practice, it was found that the $\{c_{k+}\}$ were very nearly equal for noise free simulations. The average was taken to estimate $c_{LSQ}=\text{mean}\{c_{k+}\}$. As additive noise increased, the discriminant in Eq. 4 was sometimes negative, resulting in complex-valued solutions. Therefore, the real part was used to estimate $c_{LSQ}$ and $x=x_{LSQ}+c_{LSQ}n$.

Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method for refining a preliminary estimate of a physical Bragg peak location of a pulsed ion beam delivered to a patient, the preliminary estimate of the physical Bragg peak location being derived from measured sonic signals acquired by a plurality of receivers at known locations and configured to sense thermoacoustic waves induced in the patient by the pulsed ion beam, the method of refining comprising:
   delivering the pulsed ion beam to the patient;
   simulating a dose map having a simulated Bragg peak location, the dose map corresponding to at least one planned treatment beam;
   simulating thermoacoustic emissions emanating from tissue heated by the at least one planned treatment beam as received at each of the known locations of the receivers to provide simulated sonic signals;
   pairing the measured sonic signals and the simulated thermoacoustic emissions for each of the plurality of receivers;
   for each of the pairs of the measured sonic signals and the simulated thermoacoustic emissions, determining a phase difference, $\phi_k$, and applying a Fourier shift method to infer a time shift, $\delta t_k$, between the measured and simulated sonic signal;
   for each of the plurality of receivers, computing a simulated time-of-flight between the known receiver location and the simulated Bragg peak location of the simulated dose map, $T_k$;
   for each of the plurality of receivers, computing an actual time-of-flight for each receiver location $t_k=T_k+\delta t_k$, by updating the time-of-flight between the receiver and the simulated Bragg peak location;
   computing, based on the time-of-flight for each of the known locations of the receivers, a refined physical Bragg peak location of the pulsed ion beam; and
   adapting at least one of the delivery of the pulsed ion beam and a future planned treatment based upon the refined physical Bragg peak location.

2. The method of claim 1, wherein computing the preliminary estimate of a physical Bragg peak location comprises using an acoustic beamforming technique.

3. The method of claim 2, wherein the method further comprises estimating a shift between simulated Bragg peak location and the physical Bragg peak location based on a difference in at least one of a phase and a time-of-flight, and computing the refined estimate of the physical Bragg peak location using the simulated Bragg peak location and shift between the simulated Bragg peak location and the physical Bragg peak location.

4. The method of claim 3, wherein the method further comprises estimating Bragg peak location shifts associated with each receiver of the plurality of receivers and combining the estimated Bragg peak location shifts to compute the corrected end range estimate.

5. The method of claim 1, wherein the method further comprises generating one or more ultrasound images of the target using an ultrasound system and overlaying at least the corrected end range estimate on the one or more ultrasound images.

6. The method of claim 1, where the pulsed ion beam is halted if the refined physical Bragg peak location differs from a planned target location by more than a threshold.

7. The method of claim 1, where a notification is provided to a user to reposition at least one of the plurality of receivers.

8. The method of claim 1, where an audio or visual alarm is generated when the refined physical Bragg peak location is determined unsafe.

9. The method of claim 1, where a future planned treatment is adapted based upon the refined Bragg peak location.

10. The method of claim 1, where the treatment plan is adapted in substantially real time.

11. The method of claim 10, where signals or instructions are sent to an ion delivery system.

12. The method of claim 10, where signals or instructions are sent to a positioning system to reposition a patient.

13. A system delivering a pulsed ion beam to a patient, the system comprising:

a radiation treatment system configured to deliver the pulsed ion beam to the patient;
a sonic system having a plurality of receivers configured to acquire sonic signals induced in the patient by the pulsed ion beam;
a controller programmed to:
   determine a preliminary estimate of a physical Bragg peak location of the pulsed ion beam delivered to the patient based on the sonic signals acquired by a plurality of receivers at known locations;
   simulate a dose map having a simulated Bragg peak location, the dose map corresponding to at least one planned treatment beam;
   simulate thermoacoustic emissions emanating from tissue heated by the at least one planned treatment beam as received at each of the known locations of the receivers to provide simulated sonic signals;
   pair the measured sonic signals and the simulated thermoacoustic emissions for each of the plurality of receivers;
   for each of the pairs of the measured sonic signals and the simulated thermoacoustic emissions, determining a phase difference, $\phi_k$, and applying a Fourier shift method to infer a time shift, $\delta t_k$, between the measured and simulated sonic signal;
   for each of the plurality of receivers, computing a simulated time-of-flight between the known receiver location and the simulated Bragg peak location of the simulated dose map, $T_k$;
   for each of the plurality of receivers, computing an actual time-of-flight for each receiver location $t_k = T_k + \delta t_k$, by updating the time-of-flight between the receiver and the simulated Bragg peak location;
   compute, based on the time-of-flight for each of the known locations of the receivers, a refined physical Bragg peak location of the pulsed ion beam; and
   adapt at least one of the delivery of the pulsed ion beam and a future planned treatment based upon the refined physical Bragg peak location.

14. The system of claim 13, wherein the plurality of receivers are further configured to detect sonic signals with frequencies up to approximately 300 kHz.

15. The system of claim 13, wherein the controller is further programmed to determine a difference between the times-of-flight associated with different receivers.

16. The system of claim 15, wherein the controller is further programmed to estimate a phase difference between the sonic signals in a Fourier domain to determine the difference in the times-of-flight.

17. The system of claim 13, wherein the controller is further programmed to compute a preliminary end range estimate using a beamforming technique.

18. The system of claim 13, wherein the controller is further programmed to estimate the end range by applying triangulation technique using the difference in times-of-flight corresponding to different receivers.

19. The system of claim 13, wherein the controller is further configured to communicate with an ultrasound system to generate one or more ultrasound images of the patient and to overlay the refined physical Bragg peak location on the one or more ultrasound images.

20. The system of claim 13, wherein the controller is further configured to communicate with a positioning system to reposition the patient based on the adapted treatment.

21. The system of claim 13, where the pulsed ion beam is halted if the refined physical Bragg peak location differs from a planned target location by more than a threshold.

22. The system of claim 13, where a notification is provided to a user to reposition one or more of the plurality of receivers.

23. The system of claim 13, where an audio or visual alarm is generated when the refined physical Bragg peak location is determined unsafe.

24. The system of claim 13, where the controller is configured to adapt the delivery of the pulsed ion beam in substantially real time.

25. The system of claim 24, where signals or instructions are sent to the radiation treatment system.

* * * * *